(12) United States Patent
Brennan et al.

(10) Patent No.: US 12,071,650 B2
(45) Date of Patent: Aug. 27, 2024

(54) METHOD FOR PRODUCING DOUBLE STRANDED POLYNUCLEOTIDES BASED ON OLIGONUCLEOTIDES WITH SELECTED AND DIFFERENT MELTING TEMPERATURES

(71) Applicant: EVONETIX LTD, Cambridge (GB)

(72) Inventors: Joseph Brennan, Essex (GB); Daniel Bygrave, Essex (GB); Sangeeta Aditya, Essex (GB); Raquel Sanches-Kuiper, Essex (GB)

(73) Assignee: EVONETIX LTD (GB)

( * ) Notice: Subject to any disclaimer, the term of this patent is extended or adjusted under 35 U.S.C. 154(b) by 51 days.

(21) Appl. No.: 16/493,585

(22) PCT Filed: Mar. 13, 2018

(86) PCT No.: PCT/GB2018/050634
§ 371 (c)(1),
(2) Date: Sep. 12, 2019

(87) PCT Pub. No.: WO2018/167475
PCT Pub. Date: Sep. 20, 2018

(65) Prior Publication Data
US 2021/0139957 A1    May 13, 2021

(30) Foreign Application Priority Data
Mar. 13, 2017   (GB) .................... 17160666

(51) Int. Cl.
*C12Q 1/6811*   (2018.01)
(52) U.S. Cl.
CPC ................ *C12Q 1/6811* (2013.01)

(58) Field of Classification Search
CPC ............ C12Q 1/6811; C12Q 2527/107; C12Q 2533/107; C12Q 2527/101; C12N 15/1031
See application file for complete search history.

(56) References Cited

U.S. PATENT DOCUMENTS 9,361,427 B2 *  6/2016  Hillson ................. G16B 25/00
2007/0037196 A1  2/2007  Gibson et al.
(Continued)

FOREIGN PATENT DOCUMENTS

GB    2380999 A  *  4/2003  ............. B82Y 30/00
JP    2007534303 A  *  11/2007  ............. C12N 15/10
(Continued)

OTHER PUBLICATIONS

Zampini et al. Scientific Reports. 2015. 5:11302 and Supplementary Information. (Year: 2015).*
(Continued)

*Primary Examiner* — Joseph G. Dauner
(74) *Attorney, Agent, or Firm* — BakerHostetler

(57) ABSTRACT

A method for identifying a group of single-stranded oligonucleotides for self-assembly into a double-stranded polynucleotide, the group comprising a plurality of overlapping complementary oligonucleotides, wherein each overlap between complementary oligonucleotides is selected to have a melting temperature (Tm) that differs from the melting temperatures of all other overlapping complementary oligonucleotides in the group.

15 Claims, 2 Drawing Sheets
Specification includes a Sequence Listing.

```
        A1       A2       A3       A4       A5
     _____   _____   _____   _____   _____

5'-GAACATGTCGAGCAGGTACGGCTCTCACTAGGGCCGCCGC-3'   (SEQ ID NO: 21)
3'-CTTGTACAGCTCGTCCATGCCGAGAGTGATCCCGGCGGCG-5'   (SEQ ID NO: 22)
        _____   _____   _____   _____
          B4       B3       B2       B1
```

(56) References Cited

U.S. PATENT DOCUMENTS

| | | | | |
|---|---|---|---|---|
| 2009/0305233 | A1* | 12/2009 | Borovkov | C12Q 1/6811 |
| | | | | 435/6.16 |
| 2012/0156731 | A1* | 6/2012 | Huang | C12Y 605/01001 |
| | | | | 536/23.1 |
| 2012/0259607 | A1* | 10/2012 | Hillson | G16B 25/00 |
| | | | | 703/11 |

FOREIGN PATENT DOCUMENTS

| | | | | |
|---|---|---|---|---|
| WO | WO 1999/014318 A1 | 3/1999 | | |
| WO | WO 1999/041397 A1 | 8/1999 | | |
| WO | WO 2001/079518 A2 | 10/2001 | | |
| WO | WO-03033718 A1 * | 4/2003 | | B82Y 30/00 |
| WO | WO-2004010935 A2 * | 2/2004 | | C07K 16/1027 |
| WO | WO-2004039953 A2 * | 5/2004 | | C07K 1/047 |
| WO | WO-2010071602 A1 * | 6/2010 | | C12N 15/10 |
| WO | WO 2010/132019 A1 | 11/2010 | | |
| WO | WO-2010132019 A1 * | 11/2010 | | C12N 15/1096 |

OTHER PUBLICATIONS

Birla et al. PLOS One. 2015. 10(12):e0145682. (Year: 2015).*
Stemmer et al. Gene. 1995. 164:49-53. (Year: 1995).*
Kim et al. Microelectronic Engineering. 2006. 83:1613-1616. (Year: 2006).*
Loh et al. Analytical Biochemistry. 2012. 431:54-56. (Year: 2012).*
Hoover et al. Nucleic Acids Research. 2002. 30(10):e43. (Year: 2002).*
Pengpumkiat et al. PLOS One. 2016. 11(3):e0149774. (Year: 2016).*
Birla, Bhagyashree. "Rational design and validation of DNA fragments for gene assembly based on thermodynamics" Dissertation; Iowa State University. 2017. (Year: 2017).*
Lee et al. Nucleic Acids Research. 2010. 38(8):2514-2521. (Year: 2010).*
Dormitzer et al. Science Translational Medicine. 2013. 5(185):185ra68. (Year: 2013).*
Breslauer et al.; "Predicting DNA duplex stability from the base sequence"; Proc. Natl. Acad. Sci. USA; vol. 83; Jun. 1986; p. 3746-3750.
Freier et al.; "Improved free-energy parameters for predictions of RNA duplex stability"; Proc. Natl. Acad. Sci. USA; vol. 83; Dec. 1986; p. 9373-9377.
Beaucage et al.; "Deoxynucleoside Phosphoramidites—A New Class of Key Intermediates for Deoxypolynucleotide Synthesis"; Tetrahedron Letter; vol. 22; 1981; p. 1859-1862.
Beaucage et al.; "Advances in the Synthesis of Oligonucleotides by the Phosphoramidite Approach"; Tetrahedron; vol. 48; 1992; p. 2223-2311.
Shum et al.; "Simplified methods for large scale enzymatic synthesis of oligoribonucleotides"; Nucleic Acids Research; vol. 5; Jul. 1978; p. 2297-2311.
Schott et al.; "Single-step elongation of oligodeoxynucleotides using terminal deoxynucleotidyl transferase"; Eur. J. Biochem.; vol. 143; 1984; p. 613-620.
International Patent Application No. PCT/GB2018/050634; Int'l Written Opinion and Search Report; dated May 16, 2018; 11 pages.
International Patent Application No. PCT/GB2018/050634; Int'l Preliminary Report on Patentability; dated Sep. 26, 2019; 8 pages.
Bode et al.; "TmPrime: fast, flexible oligonucleotide design software for gene synthesis"; Nucleic Acids Research; vol. 37; 2009; p. W214-W221.
Richardson et al.; "GeneDesign: Rapid, automated design of multikilobase synthetic genes"; Genome Research; vol. 16; 2006; p. 550-556.
Rouillard et al.; "Gene2Oligo: oligonucleotide design for in vitro gene synthesis"; Nucleic Acids Research; vol. 32; 2004; p. W176-W180.
Ausubel et al.; "A Compendium of Methods from Current Protocols in Molecular Biology"; Book details and Content; Short Protocols in Molecular Biology—Third Edition; John Wiley & Sons, Inc.; © 1995; 23 pages.
M J Gait; "Oligonucleotide synthesis—a practical approach"; Content; IRL Press Limited; © 1984; 9 pages.
Lilley et al.; "Methods in Enzymology DNA Structures—Part A Synthesis and Physical Analysis of DNA"; Contents; vol. 211; Academic Press, Inc.; © 1992; 5 pages.
Polak et al.; "In Situ Hybridization—Principles and Practice"; Contents; Oxford University Press; © 1992; 4 pages.
Roe et al.; "DNA Isolation and Sequencing—Essential Techniques"; Book details and Contents; John Wiley & Sons, Inc.; © 1996; 4 pages.
Sambrook et al.; "Molecular Cloning—A Laboratory Manual Second Edition"; Contents; Cold Spring Harbor Laboratory Press; © 1989; 30 pages.

* cited by examiner

METHOD FOR PRODUCING DOUBLE STRANDED POLYNUCLEOTIDES BASED ON OLIGONUCLEOTIDES WITH SELECTED AND DIFFERENT MELTING TEMPERATURES

CROSS-REFERENCE TO RELATED APPLICATIONS

This application is the National Stage of International Patent Application No. PCT/GB2018/050634, filed Mar. 13, 2018, which claims priority to European Patent Application No. 17160666.8, filed Mar. 13, 2017, the entire disclosures of both of which are incorporated herein by reference for any and all purposes.

SEQUENCE LISTING

The instant application contains a sequence listing which has been submitted electronically in ASCII format and is hereby incorporated by reference in its entirety. The ASCII copy, created on Sep. 12, 2019, is named 101705.000007 SL.txt and is 7.56 KB in size.

FIELD OF THE INVENTION

The present invention relates to the provision of polynucleotides. In particular, the invention relates to methods for identifying a group of single-stranded oligonucleotides suitable for assembly into a double-stranded polynucleotide, specifically methods which reduce the number of errors occurring during self-assembly of the polynucleotide.

BACKGROUND TO THE INVENTION

Using readily available techniques of molecular biology, it is possible to replicate and amplify polynucleotides from natural sources. Such techniques additionally enable engineering of natural nucleic acid sequences, for example through substitution, insertion or deletion of one or more nucleotides, and hence provide access to nucleic acid sequences that are not naturally available.

However, such approaches are often time-consuming and labour intensive. In addition, a reliance on natural sequences as a starting point may limit the scope of sequences that are practically achievable. Furthermore, difficulty in accessing natural polynucleotides themselves may give rise to additional obstacles.

De novo synthesis of polynucleotides offers a route to theoretically any nucleic acid sequence and may therefore overcome some of the issues with traditional molecular biology-based approaches.

In vitro synthesis of relatively short oligonucleotides, for example via solid-phase synthesis using the phosphoramidite method, is well known. Indeed, traditional molecular biology often relies on synthesised oligonucleotide primers for use in polymerase chain reaction (PCR) and site-directed mutagenesis methods.

However, typical oligonucleotide synthesis techniques do not give rise to 100% yields for each nucleotide addition step. Such imperfect yields combine exponentially over the length of a nucleic acid sequence and lead to significant difficulties in the provision of longer polynucleotides, such as full length genes and genomes, due to very low overall yields. In addition, the accumulating probability of errors from each addition step may cause further problems with accurately synthesising polynucleotides using such methods.

Polynucleotides may be synthesised by connecting a number of separately synthesised oligonucleotides. Typically under this approach, a group of oligonucleotides is synthesised, for example using automated solid-phase synthesis, purified and the individual oligonucleotides are subsequently connected together by annealing and ligation or polymerase reactions.

However, annealing approaches such as this may give rise to erroneous product polynucleotides due to the annealing of non-perfectly complementary oligonucleotides. The potential for such errors increases with increasing polynucleotide length, and may give rise to serious difficulties in accessing larger sequences.

Attempts to address issues with inaccurate annealing have been previously based on sequential mixing and annealing of one oligonucleotide at a time to facilitate correct pairing of complementary oligonucleotides. However, these approaches are time-consuming and there remains a significant need in the art for methods of accurately providing polynucleotides, in particular those of whole gene and genome scale.

SUMMARY OF THE INVENTION

The present inventors have developed an improved method for providing a polynucleotide, which comprises designing a group of oligonucleotides that is suitable for self-assembly into a polynucleotide in a manner which mitigates errors occurring during self-assembly.

The method disclosed herein is based on intelligently selecting the overlapping regions of opposing oligonucleotides (e.g. from the sense and anti-sense strands), which are suitable for self-assembly, to achieve a spread of melting temperatures. The spread of melting temperatures can be achieved, for example, by taking into account the effects of overlap length and sequence content on melting temperature. The resulting group of oligonucleotides will thereby undergo sequential self-assembly into a polynucleotide structure in a temperature-controlled environment.

Accordingly, in one aspect the invention provides a method for identifying a group of single-stranded oligonucleotides for self-assembly into a double-stranded polynucleotide, the group comprising a plurality of overlapping complementary oligonucleotides, wherein each overlap between complementary oligonucleotides is selected to have a melting temperature ($T_m$) that differs from the melting temperatures of all other overlapping complementary oligonucleotides in the group.

In one embodiment, the group of oligonucleotides corresponds to the entirety of the sequences of both strands of the polynucleotide.

In another embodiment, the group of oligonucleotides does not form the entirety of the sequences of both strands of the polynucleotide (i.e. one or more gaps are present in one or both strands, with the proviso that the gaps in opposing strands do not overlap (i.e. coincide)). The omitted sequence regions of the double-stranded polynucleotide may be added during synthesis using a nucleic acid polymerase (e.g. using polymerase chain assembly, PCA; for example using a DNA polymerase, such as a 5'-3' DNA polymerase)).

In an alternative embodiment, one or more of the single-stranded oligonucleotides, preferably all of the single-stranded oligonucleotides, are single-stranded oligonucleotide overhangs (i.e. single-stranded oligonucleotide overhang at an end of an oligonucleotide with a double-stranded region). Thus, for example, the double-stranded polynucleotide may be assembled using a group of oligonucleotides that each have double-stranded regions and one or two single-stranded overhangs.

In another aspect, the invention provides a method for identifying a group of single-stranded oligonucleotides for assembly into a double-stranded polynucleotide comprising the steps:
(a) dividing one strand of the polynucleotide to form a first set of oligonucleotides; and
(b) dividing the opposite strand of the polynucleotide to form a second set of oligonucleotides;
wherein each of the oligonucleotides of the second set of oligonucleotides overlaps with two oligonucleotides of the first set of oligonucleotides, except that two oligonucleotides at a 5' or 3' end of the double-stranded polynucleotide overlaps with only one complementary oligonucleotide, and wherein each overlap between complementary oligonucleotides is selected to have a melting temperature ($T_m$) that differs from the melting temperatures of all other overlapping complementary oligonucleotides in the group.

In one embodiment, the first set of oligonucleotides corresponds to the entire sequence of one strand of the polynucleotide, when positioned together end-to-end, and the second set of oligonucleotides corresponds to the entire sequence of the opposite strand of the polynucleotide, when positioned together end-to-end.

In another embodiment, step (a) and/or (b) comprise introducing one or more gaps in the sequence of the one and/or opposite strand of the polynucleotide, with the proviso that gaps in opposing strands do not overlap (i.e. coincide). Put another way, in one embodiment the double-stranded polynucleotide assembled from the group of oligonucleotides has one or more gaps in the sequence of one or both strands, with the proviso that gaps in opposing strands do not overlap (i.e. coincide). The omitted sequence regions of the double-stranded polynucleotide may be added during synthesis using a nucleic acid polymerase (e.g. using polymerase chain assembly, PCA; for example using a DNA polymerase, such as a 5'-3' DNA polymerase)).

In another aspect, the invention provides a method for providing multiple copies of a double-stranded polynucleotide comprising the steps:
(a) providing a group of oligonucleotides identified using the method of the invention; and
(b) hybridising the oligonucleotides.

In another aspect, the invention provides a method for providing multiple copies of a double-stranded polynucleotide comprising the steps:
(a) providing a first set of oligonucleotides corresponding to one strand of the polynucleotide, preferably corresponding to one entire strand; and
(b) providing a second set of oligonucleotides corresponding to the opposite strand of the polynucleotide, preferably corresponding to the entire opposite strand,
wherein each of the oligonucleotides of the second set of oligonucleotides overlaps with two oligonucleotides of the first set of oligonucleotides, except that two oligonucleotides at a 5' or 3' end of the double-stranded polynucleotide overlaps with only one complementary oligonucleotide, and
wherein each overlap between complementary oligonucleotides is selected to have a melting temperature ($T_m$) that differs from the melting temperatures of all other overlapping complementary oligonucleotides in a group consisting of the first and second sets of oligonucleotides; and
(c) hybridising the first and second set of oligonucleotides.

Which strand of the polynucleotide that is used to identify the first or second set of oligonucleotides is arbitrary. In one embodiment, the first set of oligonucleotides corresponds to the sense (positive strand) and the second set of oligonucleotides corresponds to the anti-sense (negative strand). In another embodiment, the second set of oligonucleotides corresponds to the sense (positive strand) and the first set of oligonucleotides corresponds to the anti-sense (negative strand).

In a preferred embodiment, the hybridising comprises annealing the oligonucleotides.

In one embodiment, the hybridising comprises heating the oligonucleotides to a temperature greater than or equal to the highest $T_m$ (preferably greater than the highest $T_m$) for about 10 seconds to 5 minutes, 10 seconds to 4 minutes, 10 seconds to 3 minutes, 10 seconds to 2 minutes, 10 seconds to 1 minutes or 10-30 seconds.

In one embodiment, the hybridising comprises decreasing the temperature from a starting temperature over a period of time. Preferably, the starting temperature is greater than or equal to the highest $T_m$, preferably greater than the highest $T_m$. Preferably, the hybridising comprises decreasing the temperature from a starting temperature to a temperature less than or equal to the lowest $T_m$, preferably less than the lowest $T_m$.

In a preferred embodiment, the hybridising comprises decreasing the temperature from a temperature greater than or equal to the highest $T_m$ to a temperature less than or equal to the lowest $T_m$. In another preferred embodiment, the hybridising comprises decreasing the temperature from a temperature greater than the highest $T_m$ to a temperature less than the lowest $T_m$.

In one embodiment, the starting temperature is less than or equal to about 95° C., 90° C., 85° C., 80° C., 75° C., 70° C., 65° C., 60° C., 55° C. or 50° C., preferably less than or equal to about 95° C.

In one embodiment, the starting temperature is about 50-95° C., 55-95° C., 60-95° C., 65-95° C., 70-95° C., 75-95° C., 80-95° C., 85-95° C. or 90-95° C. In another embodiment, the starting temperature is about 50-90° C., 55-90° C., 60-90° C., 65-90° C., 70-90° C., 75-90° C., 80-90° C. or 85-90° C. Preferably, the starting temperature is about 90-95° C.

In one embodiment, the period of time over which the temperature is decreased is about 1 minute to 12 hours, 1 minute to 6 hours, 1 minute to 3 hours, 1 minute to 1 hour, 1-45 minutes, 1-30 minutes, 1-15 minutes, 1-10 minutes or 1-5 minutes. Preferably, the period of time is about 1-5 minutes.

In one embodiment, the temperature is decreased at a rate of about 0.1-10° C./minute, 0.1-5° C./minute, 0.1-2° C./minute or 0.5-1.5° C./minute, preferably 0.5-1.5° C./minute.

In one embodiment, the temperature is decreased at a rate of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.0° C./minute, preferably at a rate of about 1° C./minute.

In one embodiment, the hybridising comprises decreasing the temperature to a temperature less than or equal to about 21° C.

In one embodiment, the temperature is decreased continuously. In another embodiment, the temperature is decreased in a plurality of steps.

In one embodiment, the hybridising comprises one or more cycles of decreasing the temperature (e.g. from a temperature greater than or equal to the highest $T_m$ to a temperature less than or equal to the lowest $T_m$, preferably from a temperature greater than the highest $T_m$ to a temperature less than the lowest $T_m$) followed by increasing the temperature (e.g. from a temperature less than or equal to the lowest $T_m$ to a temperature greater than or equal to the highest $T_m$, preferably from a temperature less than the lowest $T_m$ to a temperature greater than the highest $T_m$). The final cycle of temperature change in this embodiment is preferably followed by the further step of decreasing the temperature (e.g. to a temperature less than or equal to the lowest $T_m$, preferably to a temperature less than the lowest $T_m$).

In another embodiment, the hybridising comprises decreasing the temperature (preferably from a temperature greater than or equal to the highest $T_m$ to a temperature less than or equal to the lowest $T_m$, preferably from a temperature greater than the highest $T_m$ to a temperature less than the lowest $T_m$) with the proviso that the temperature is cycled around one or more (preferably all) of the melting temperatures. By "cycled around one or more of the melting temperatures", it is to be understood that for each of the one or more melting temperatures the temperature is decreased from above the melting temperature to below the melting temperature, and then one or more cycles of increasing the temperature to above the melting temperature followed by decreasing the temperature to below the melting temperature are carried out.

By way of example only, if the $T_m$=75.5° C. then the cycle could be enacted by lowering the temperature to 75° C. or lower then increasing the temperature to 76° C. or higher, preferably looping this cycle several times; then the temperature change could move to the next lowest $T_m$.

In a preferred embodiment, the method further comprises the step of admixing the entire group of oligonucleotides before the hybridising step. In another preferred embodiment, the oligonucleotides are admixed in subsets, which are hybridised separately, and the subsets are then admixed together and hybridised.

In one embodiment, the oligonucleotides are less than or equal to about 250, 200, 175, 150, 125, 100, 75, 50 or 25 nucleotides in length, preferably less than or equal to about 200 nucleotides in length.

In one embodiment, the oligonucleotides are greater than or equal to about 4, 5, 6, 7, 8, 9, 10 or 15 nucleotides in length, preferably greater than or equal to about 4 nucleotides in length.

In one embodiment, the polynucleotide is less than or equal to about 500, 400, 300, 200, 100, 50 or 25 kbp in length.

In one embodiment, the polynucleotide is less than or equal to about 10000, 7500, 5000, 4500, 4000, 3500, 3000 or 2500 bp in length.

In one embodiment, the overlaps are selected to provide a highest $T_m$ of less than or equal to about 95° C., 90° C., 85° C., 80° C., 75° C., 70° C., 65° C., 60° C., 55° C. or 50° C., preferably less than or equal to about 95° C.

In one embodiment, the overlaps are selected to provide a highest $T_m$ of about 50-95° C., 55-95° C., 60-95° C., 65-95° C., 70-95° C., 75-95° C., 80-95° C., 85-95° C. or 90-95° C. In another embodiment, the overlaps are selected to provide a highest $T_m$ of about 50-90° C., 55-90° C., 60-90° C., 65-90° C., 70-90° C., 75-90° C., 80-90° C. or 85-90° C.

In one embodiment, the overlaps are selected to provide a lowest $T_m$ of greater than or equal to about 10° C., 11° C., 12° C., 13° C., 14° C., 15° C., 16° C., 17° C., 18° C., 19° C., 20° C. or 21° C., preferably greater than or equal to about 10° C.

In a preferred embodiment, each overlap is selected to provide a range of melting temperatures, wherein the difference between each melting temperature and its nearest neighbour melting temperature (i.e. the closest higher and/or lower $T_m$) is as great as possible.

In one embodiment, each overlap is selected to provide a difference between its $T_m$ and the closest higher and/or lower $T_m$ (i.e. its nearest neighbour $T_m$) of greater than or equal to about 0.5° C., 1° C., 2° C., 3° C., 4° C., 5° C., 6° C., 7° C., 8° C., 9° C. or 10° C., preferably greater than or equal to about 1° C.

In one embodiment, each overlap is selected to provide a difference between its $T_m$ and the closest higher and/or lower $T_m$ of about 0.5-10° C., 0.5-9° C., 0.5-8° C., 0.5-7° C., 0.5-6° C., 0.5-5° C., 0.5-4° C., 0.5-3° C., 0.5-2° C. or 0.5-1° C., preferably about 0.5-5° C. In another embodiment, each overlap is selected to provide a difference between its $T_m$ and the closest higher and/or lower $T_m$ of about 1-10° C., 1-9° C., 1-8° C., 1-7° C., 1-6° C., 1-5° C., 1-4° C., 1-3° C. or 1-2° C., preferably about 1-5° C. In another embodiment, each overlap is selected to provide a difference between its $T_m$ and the closest higher and/or lower $T_m$ of about 0.5-10° C., 1-9° C. 2-8° C., 3-7° C. or 4-6° C., preferably about 4-6° C.

In one embodiment, the oligonucleotides are synthesised in vitro. In one embodiment, the oligonucleotides are synthesised using a method of solid-state synthesis, for example using a method based on solid-state phosphoramidite chemistry. In one embodiment, the oligonucleotides are synthesised using enzymatic coupling.

In one embodiment, the method further comprises the step of polymerase chain assembly (PCA). The PCA may be carried out by, for example, treating the hybridised oligonucleotides with a nucleic acid polymerase (e.g. a DNA polymerase, such as a 5'-3' DNA polymerase). The PCA may be used to add any omitted sequence regions of the double-stranded polynucleotide (i.e. corresponding to sequence gaps between neighbouring oligonucleotides).

In one embodiment, the method further comprises the step of treating the hybridised oligonucleotides with a nucleic acid polymerase, preferably a DNA polymerase (e.g. a 5'-3' DNA polymerase).

In one embodiment, the method further comprises the steps:
  (d) treating the hybridised oligonucleotides with a ligase and optionally a polynucleotide kinase; and/or
  (e) amplifying the double-stranded polynucleotide.

In one embodiment, the double-stranded polynucleotide is a DNA, RNA or XNA.

In one embodiment, the double-stranded polynucleotide comprises a coding region. In another embodiment, the double-stranded polynucleotide is a non-coding nucleic acid (i.e. the polynucleotide does not comprise a coding region).

In one embodiment, the double-stranded polynucleotide comprises an expression construct, chromosome or genome.

In one embodiment, the expression construct is a bacterial, mammalian or viral expression construct.

In a preferred embodiment, the number of errors in assembly of the polynucleotide due to hybridising of non-complementary oligonucleotides is reduced in comparison to a method in which each overlap between complementary oligonucleotides is not selected to have a melting temperature ($T_m$) that differs from the melting temperatures of all other overlapping complementary oligonucleotides in the group. In one embodiment, the number of errors is reduced by greater than or equal to 5%, 10%, 20%, 30%, 40%, 50%, 60%, 70%, 80%, 90% or 95% in comparison to a method in which each overlap between complementary oligonucleotides is not selected to have a melting temperature ($T_m$) that differs from the melting temperatures of all other overlapping complementary oligonucleotides in the group.

In another aspect, the invention provides a group of single-stranded oligonucleotides for self-assembly into a double-stranded polynucleotide, the group comprising a plurality of overlapping complementary oligonucleotides, wherein each overlap between complementary oligonucleotides is selected to have a melting temperature ($T_m$) that differs from the melting temperatures of all other overlapping complementary oligonucleotides in the group.

The oligonucleotides, polynucleotides and/or overlaps may be as defined herein.

In another aspect, the invention provides a double-stranded polynucleotide produced by the method of the invention.

In one embodiment, the selection of the oligonucleotides is carried out by a computer.

In another aspect, the invention provides a data processing device comprising means for carrying out the method of the invention.

In another aspect, the invention provides a computer program product in which a computer program is stored in a non-transient fashion, which when executed on a processing device causes the processing device to carry out the method of the invention.

In another aspect, the invention provides a computer-readable medium comprising instructions which, when executed by a computer, cause the computer to carry out the method of the invention.

Figure 1:
FIG. 1

An example double-stranded DNA constructed of 9 oligonucleotides. Each strand is comprised of a number of separate oligonucleotides, which are represented by differing text formats (plain text, underline, bold and/or italic). The top strand is comprised of 5 oligonucleotides (A1-A5) and the bottom strand is comprised of 4 oligonucleotides (B1-B4).

FIG. 2

Spread of melting temperatures achieved with a group of oligonucleotides identified from a nucleic acid sequence encoding green fluorescent protein (GFP).

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

Nucleic Acids

The invention relates to the provision of polynucleotides. In particular, the invention relates to methods for identifying a group of single-stranded oligonucleotides suitable for assembly into a double-stranded polynucleotide, specifically methods which reduce the number of errors occurring during self-assembly of the polynucleotide.

The methods of the invention enable the creation of polynucleotides, such as genes, genomes and chromosomes starting from information only, i.e. the invention may provide polynucleotides without a requirement for existing nucleic acid molecules, such as genes or genomes.

The methods of the invention are not particularly limited to the type of nucleic acid to be provided. For example, the nucleic acid (e.g. oligonucleotide and/or polynucleotide) may be a deoxyribonucleic acid (DNA), ribonucleic acid (RNA) or xeno nucleic acid (XNA).

In one embodiment, the nucleic acid (e.g. oligonucleotide and/or polynucleotide) is a DNA. In one embodiment, the nucleic acid (e.g. oligonucleotide and/or polynucleotide) is a RNA. In one embodiment, the nucleic acid (e.g. oligonucleotide and/or polynucleotide) is a XNA.

Xeno nucleic acid (XNA) is a synthetic nucleic acid that is an artificial alternative to DNA and RNA. As with DNA and RNA, XNA is an information-storing polymer, however XNA differs to DNA and RNA in the structure of the sugar-phosphate backbone. By 2011, at least six synthetic sugars had been used to create XNA backbones that are capable of storing and retrieving genetic information. Substitution of the backbone sugars make XNAs functionally and structurally analogous to DNA and RNA.

The term "oligonucleotide" as used herein may refer to short nucleic acid polymers, for example polymers of DNA, RNA or XNA nucleotides. Although the exact length of an oligonucleotide is not particularly limited, an oligonucleotide may be, for example, about 4-200 nucleotides in length.

The term "polynucleotide" as used herein may refer to longer nucleic acid polymers, for example polymers of DNA, RNA or XNA nucleotides.

The term "nucleotide" as used herein may refer to nucleotides, such as DNA and RNA nucleotides, as well as nucleotide analogues.

The term "hybridisation" as used herein refers to the hydrogen bonding of opposing nucleic acid strands, preferably Watson-Crick hydrogen bonding between complementary nucleoside or nucleotide bases.

Nucleotides each comprise a nucleobase. The term "nucleobase" as used herein refers to nitrogenous bases, including purines and pyrimidines, such as the DNA nucleobases A, T, G and C, the RNA nucleobases A, U, C and G, as well as non-DNA/RNA nucleobases, such as 5-methylcytosine ($^{Me}C$), isocytosine, pseudoisocytosine, 5-bromouracil, 5-propynyluracil, 5-propyny-6-fluorouracil, 5-methylthiazoleuracil, 6-aminopurine, 2-aminopurine, inosine, 2,6-diaminopurine, 7-propyne-7-deazaadenine, 7-propyne-7-deazaguanine and 2-chloro-6-aminopurine.

Nucleic acids may be, for example, single- or double-stranded.

The "sense" strand ("positive" strand) has the same sequence as the messenger RNA into which the double-stranded polynucleotide is transcribed (with the exception of any typical nucleobases differences, e.g. between DNA and RNA, T is replaced by U). The opposite, "anti-sense" strand ("negative" strand) is used as the template for messenger RNA during transcription. The anti-sense strand is thus responsible for the RNA that may be, for example, translated to protein, while the sense strand possesses a nearly identical makeup to that of the messenger RNA.

Complementarity is the principle affecting the binding of two single-stranded nucleic acids to form a double-stranded nucleic acid. It is a property shared between two nucleic acid sequences, such that when they are aligned antiparallel to each other, the nucleotides opposing each other in the two sequences will all be complementary for optimal binding. At the molecular level, complementarity is determined by optimal hydrogen bonding between specific base pairs. For example, in DNA, adenine is complementary to thymine, and guanine is complementary to cytosine; and in RNA, adenine is complementary to uracil, and guanine is complementary to cytosine. Complementary pairing of bases allows information to be copied from one molecule to another, and, in nature, from one generation of cells to another.

A double-stranded nucleic acid may be comprised of two strands of the same length, in which case both ends of the double-stranded nucleic acid may be blunt ended.

Alternatively, one or both ends of a double-stranded nucleic acid may exhibit an overhang of single-stranded nucleic acid, for example if one strand is longer than the other or if the two strands are offset from one another. Such overhangs may enable a single-stranded nucleic acid to bind to two or more complementary nucleic acids, and thus, by the same token, the double-stranded nucleic acid may bind to one or more further single-stranded nucleic acids by virtue of base pairing with the overhang, thus creating regions of overlap between opposing single-stranded nucleic acids.

These concepts are illustrated by way of example only in FIG. 1, which depicts an example double-stranded DNA comprised of 9 oligonucleotides. Each strand is comprised of a number of separate oligonucleotides, which are represented in the figure by differing text formats (plain text, underline, bold and/or italic). The top strand is comprised of 5 oligonucleotides (A1-A5) and the bottom strand is comprised of 4 oligonucleotides (B1-134). In this example, the top and bottom strands are complementary and, for example, oligonucleotide A2 overlaps with oligonucleotides B3 and B4, having regions of complementarity with each of B3 and B4.

Identification of Oligonucleotides

In one aspect the invention provides a method for identifying a group of single-stranded oligonucleotides for assembly (in particular, self-assembly) into a double-stranded polynucleotide, the group comprising a plurality of overlapping complementary oligonucleotides, wherein each overlap between complementary oligonucleotides is selected to have a melting temperature ($T_m$) that differs from the melting temperatures of all other overlapping complementary oligonucleotides in the group.

In another aspect, the invention provides a method for identifying a group of single-stranded oligonucleotides for assembly (in particular, self-assembly) into a double-stranded polynucleotide comprising the steps:
  (a) dividing one strand of the polynucleotide to form a first set of oligonucleotides; and
  (b) dividing the opposite strand of the polynucleotide to form a second set of oligonucleotides;
  wherein each of the oligonucleotides of the second set of oligonucleotides overlaps with two oligonucleotides of the first set of oligonucleotides, except that two oligonucleotides at a 5' or 3' end of the double-stranded polynucleotide overlaps with only one complementary oligonucleotide, and wherein each overlap between complementary oligonucleotides is selected to have a melting temperature ($T_m$) that differs from the melting temperatures of all other overlapping complementary oligonucleotides in the group.

Preferably, the methods are carried out in an automated manner, for example the methods of the invention may be implemented using a computer.

Intelligent selection of the overlapping regions of the opposing strands using a method of the invention provides a spread of melting temperatures across all the overlaps. As a result, the group of oligonucleotides may undergo sequential assembly into a double-stranded polynucleotide structure in a temperature-controlled environment (i.e. not all oligonucleotides will hybridise at the same time). This is advantageous over alternative methods that do not select the overlapping regions of the opposing strands to achieve a spread of melting temperatures, because the sequential assembly reduces the number of errors occurring, for example due to hybridisation of non-complementary oligonucleotides.

Put another way, in the methods of the invention, each overlap is selected so that there is a difference between its $T_m$ and the nearest neighbour $T_m$ (i.e. the closest higher and/or lower $T_m$). Preferably, the difference is greater than or equal to about 0.5° C., 1° C., 2° C., 3° C., 4° C., 5° C., 6° C., 7° C., 8° C., 9° C. or 10° C., preferably greater than or equal to about 1° C.

In a preferred embodiment, all the overlaps are selected to provide a range of melting temperatures, wherein the difference between each $T_m$ and its nearest neighbour $T_m$ is as great as possible.

The spread of melting temperatures can be achieved, for example, by taking into account the effects of overlap length and sequence content on melting temperature of the oligonucleotides to be assembled.

By way of example, the following method may be carried out to identify a group of oligonucleotides that are suitable for assembly of a double-stranded polynucleotide, in particular in a temperature-controlled manner.

First, a number of criteria may be established as parameters to guide the search for a solution group of oligonucleotides, for example:
  Maximum oligonucleotide length: 200
  Minimum oligonucleotide length: 4
  Minimum melt point considered: 10° C.
  Maximum melt point considered: 90° C.
  Minimum delta between melt temperature points: 1° C.

The following additional optional criteria may also be adopted to give structure to the search:
  Ideal delta between melt temperature points: 5° C.

The search for a solution may then be carried out using the following algorithm:
  1. Divide the temperature range into n points by having a point at each ideal delta increment between the maximum and minimum melting temperature (as shown below, the order of this list is significant), e.g. for the example parameters above:
     [90, 85, 80, 75, 70, 65, 60, 55, 50, 45, 40, 35, 30, 25, 20, 15, 10]° C.
  2. Break up the target polynucleotide sequence into overlap regions from the 3' direction, such that the melt temperature is as close to 90° C. as possible.
  3. Repeat step 2, targeting the next melt temperature point in the list established in step 1 (i.e. 85° C., then 80° C., 75° C.) and so on until all melt temperature points in the list established in step 1 have an overlap associated with them.

4. Calculate the spread of melt temperatures in the solution and stop if it satisfies the previously established criteria.
5. If no satisfactory solution is found, reorder the list established in step 1 systematically and repeat the algorithm until either all list orders are exhausted or a solution is found.

This example method may generate a number of possible solutions for a target sequence, however, it may only be necessary to find the first solution that satisfies the set criteria.

The parameters recited in the above method are by way of example only, and may be adjusted as appropriate.

Codon Optimisation and Secondary Structure

The sequences of the overlaps, oligonucleotides and/or polynucleotides may be codon-optimised (i.e. the nucleic acid sequence may be altered, taking advantage of redundancy in the genetic code). Codon-optimisation may be used to achieve increased or decreased expression of an encoded product. However, codon-optimisation may be used to achieve alternative nucleic acid sequences that encode the same product (e.g. protein sequence), but which have a different melt profile. This may be beneficial to achieve an optimal spread of melting temperatures, for example if one or more melting temperatures clash.

Codon optimisation has previously been described in WO 1999/041397 and WO 2001/079518. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

The methods of the invention may also comprise analysis of nucleic acid secondary structure. In one embodiment, the methods of the invention may further comprise selecting the oligonucleotides to reduce or minimise the probability of secondary structure. In another embodiment, the methods of the invention may further comprise selecting the oligonucleotides to increase the probability of their forming any secondary structure. The latter may be particularly beneficial for nucleic acid origami applications.

Melting Temperature ($T_m$)

The melting temperature ($T_m$) of a nucleic acid sequence is the temperature at which 50% of the nucleic acid and its complement are in duplex form.

The melting temperature of a nucleic acid sequence may be determined empirically. For example, a single-stranded nucleic acid and its complement may be introduced into a cell in a temperature-controlled UV spectrophotometer. Variation in UV absorbance at a suitable wavelength (e.g. 260 nm) may then be measured as a function of temperature, which will typically give rise to an S-shaped curve with two plateaus. The melting temperature may then be determined as the temperature at the point on the melting curve that is half-way between the two plateaus.

Although empirical means may be an accurate manner of determining melting temperatures, these experiments are typically time-consuming. Alternatively, melting temperatures may be calculated using any of a number of formulae that have been developed for this purpose and the skilled person will be readily able to select a suitable method.

A number of formulae have been developed that enable calculation of melting temperatures based solely on nucleotide content of a nucleic acid sequence. By way of example, the following formula may be used to calculate the melting temperature of a nucleic acid:

$$T_m = 4 \times (G+C) + 2 \times (A+T)$$

where: G, C, A and T are the number of occurrences of each nucleotide.

An alternative example formula for calculating the melting temperature of a nucleic acid is:

$$T_m = 64.9 + \frac{41 \times (G + C - 16.4)}{(A + T + G + C)}$$

where: G, C, A and T are the number of occurrences of each nucleotide.

Factors other than nucleotide content may affect the melting temperature of a nucleic acid in solution, such as nucleic acid strand concentration, salt concentration and the concentration of any denaturants, such as formamide or DMSO. Further formulae have been developed which take account of such factors. By way of example, the following formula, which comprises a salt concentration adjustment, may be used to calculate the melting temperature of a nucleic acid:

$$T_m = 4 \times (G+C) + 2 \times (A+T) - 16.6 \times \log_{10} 0.050 + 16.6 \times \log_{10} [Na^+]$$

where: G, C, A and T are the number of occurrences of each nucleotide.

An alternative example formula, which comprises a salt concentration adjustment, for calculating the melting temperature of a nucleic acid is:

$$T_m = 100.5 + \left(\frac{41 \times (G+C)}{(A+T+G+C)}\right) - \left(\frac{820}{(A+T+G+C)}\right) + 16.6 \times \log_{10}[Na^+]$$

where: G, C, A and T are the number of occurrences of each nucleotide.

Although these example formulae refer to DNA bases, similar formulae may be equally applicable to other nucleic acids, such as RNA.

Other approaches may be based on the use of thermodynamic calculations to determine melting temperatures. From observation of melting temperatures it is possible to experimentally determine the associated thermodynamic parameters ($\Delta G$, $\Delta H$ and $\Delta S$) for nucleic acid sequences and, vice versa, when the thermodynamic parameters of a given nucleic acid sequence are known it is possible to predict the melting temperature of the sequence.

The nearest-neighbour model provides an accurate means for determining the thermodynamic parameters for a given nucleic acid sequence and therefore can be used to predict melting temperatures. This model is based on the understanding that the interaction between bases on different strands may also depend on the neighbouring bases. For example, instead of treating a nucleic acid duplex as a number of interactions between base pairs, the nearest-neighbour model treats the duplex as a number of interactions between "neighbouring" base pairs. Empirically determined thermodynamic basis sets for all possible nearest neighbour interactions (e.g. for DNA, see Breslauer, K. J. et al. (1986) Proc. Natl. Acad. Sci. USA 83: 3746-3750; and for RNA, see Freier, S. M. et al. (1986) Proc. Natl. Acad. Sci. USA 83: 9373-9377) may thus be used to calculate the thermodynamic parameters for a specific sequence and hence predict the melting temperature of that sequence.

The methods of the invention may use, for example, any one of the above methods of determining melting temperature. The melting temperatures of all the overlaps are preferably all determined using the same method of determining melting temperature. Corrections may be applied, for example, due to salt and/or nucleic acid concentrations, chain to form the oligonucleotide product. The oligonucleotide chain is typically anchored at one end to a suitable solid support.

The terminal protecting group (e.g. 5'-DMT) may be retained or removed depending on the subsequent purification method. The oligonucleotide may then be cleaved from the solid support prior to purification, typically by treatment with ammonium hydroxide, which also serves to remove base and phosphate triester protecting groups.

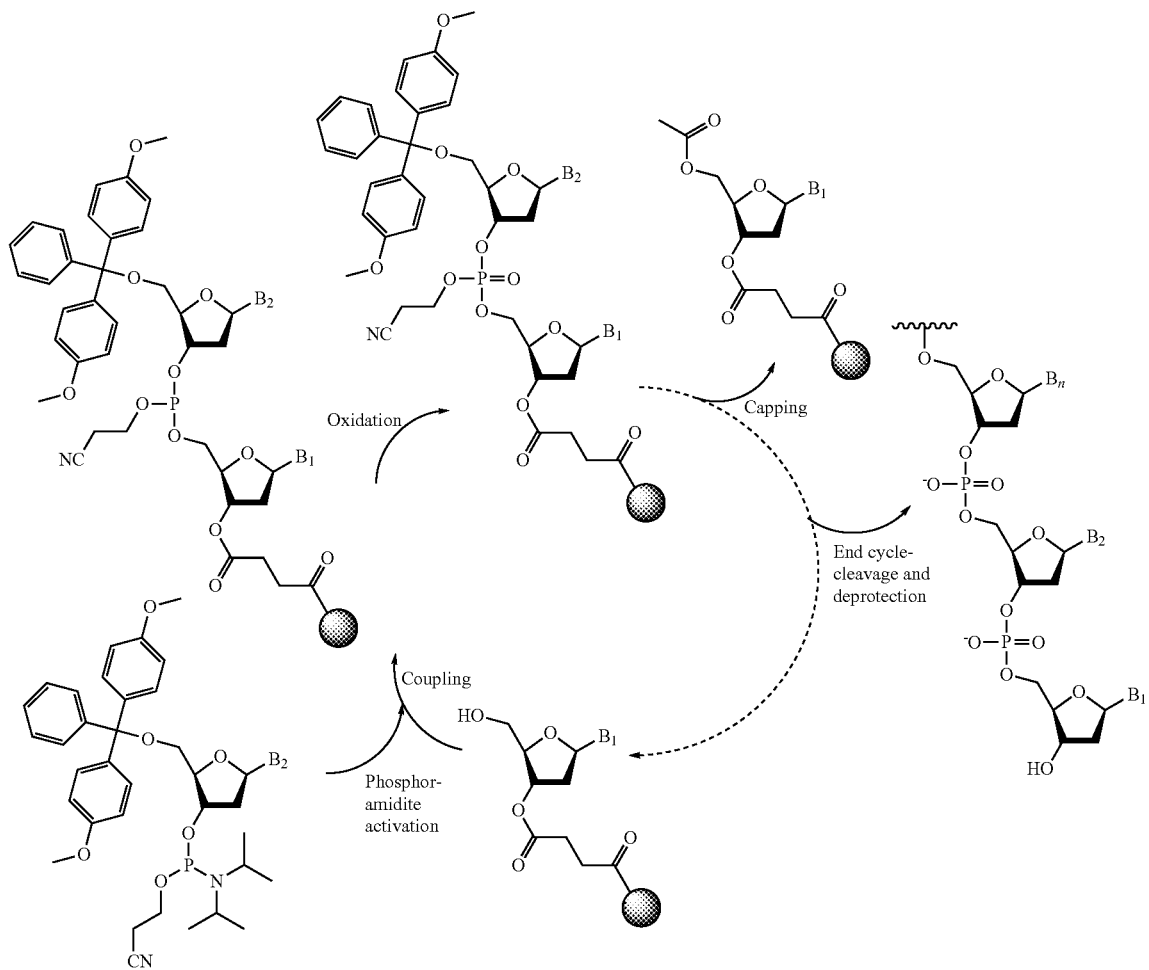

Scheme 1 which the skilled person would readily be able to apply based on approaches known in the art.

Preparation of Oligonucleotides

Oligonucleotides may be prepared, for example, using solution- or solid-phase approaches. Oligonucleotides are typically synthesised using phosphoramidite coupling chemistry (Beaucage et al. (1981) Tetrahedron Lett. 22: 1859; Beaucage et al. (1992) Tetrahedron 48: 2223-2311), the general synthetic strategy for which is illustrated in Scheme 1 below.

Phosphoramidite-based synthesis of oligonucleotides involves activation of nucleoside phosphoramidite monomer precursors by reaction with an activating agent to form activated intermediates, followed by sequential addition of the activated intermediates to the growing oligonucleotide High throughput oligonucleotide synthesis can be achieved using an automated synthesiser.

Downstream oligonucleotide purification is typically achieved using reverse phase (RP) purification or anion exchange (AX) chromatography. Other chromatographic techniques suitable for small-scale purification of oligonucleotides include hydrophobic interaction chromatography (HIC), affinity chromatography, gel permeation chromatography, mixed-mode chromatography (e.g. ion-paired RP, hydroxyapetite, slalom chromatography) and the use of stationary phases that combine anion exchange and RP characteristics.

As alternatives to phosphoramidite coupling approaches, enzymatic coupling methods may also be used to synthesise oligonucleotides. Example enzymatic methods include the "uncontrolled" and "blocked" methods described herein.

The "uncontrolled" method may use a polymerase, such as a template-independent polymerase or a nucleotidyl transferase to add a desired nucleotide to extend an existing oligonucleotide. The product of each extension step is a mixture of oligonucleotides in which different numbers of the nucleotide have been added (i.e. [starting oligonucleotide]+(n) nucleotides, wherein n=0, 1, 2, 3 etc.). The desired extension product may then be purified from the reagents and side-products. Nucleotidyl transferase incubation and oligonucleotide purification steps may be repeated until the final oligonucleotide is reached. Example nucleotidyl transferases include polynucleotide phosphorylase (Shum et al. (1978) Nucleic Acids Res. 5: 2297-2311) and terminal deoxynucleotidyl transferase (Schott et al. (1984) Eur. J. Biochem. 143: 613-620). The "blocked" method is an adaptation of this, in which the nucleotide reagent used in the extension step is blocked to prevent addition of more than one nucleotide during the enzymatic extension step. After the extension step, the product may be purified and the blocking group removed.

Preparation of Polynucleotides

Provision of a target polynucleotide from a group of oligonucleotides identified according to a method of the invention takes advantage of molecular self-assembly. Self-assembly is a process by which molecules naturally adopt a defined arrangement. In the context of the present invention, individual oligonucleotides will naturally hybridise with complementary oligonucleotides with which they overlap, thus functioning as building blocks that link together to form a product polynucleotide.

In one aspect, the invention provides a method for providing multiple copies of a double-stranded polynucleotide comprising the steps:
  (a) providing a group of oligonucleotides identified using the method of the invention; and
  (b) hybridising the oligonucleotides.

In another aspect, the invention provides a method for providing multiple copies of a double-stranded polynucleotide comprising the steps:
  (a) providing a first set of oligonucleotides corresponding to one strand of the polynucleotide, preferably corresponding to one entire strand; and
  (b) providing a second set of oligonucleotides corresponding to the opposite strand of the polynucleotide, preferably corresponding to the entire opposite strand, wherein each of the oligonucleotides of the second set of oligonucleotides overlaps with two oligonucleotides of the first set of oligonucleotides, except that two oligonucleotides at a 5' or 3' end of the double-stranded polynucleotide overlaps with only one complementary oligonucleotide, and
  wherein each overlap between complementary oligonucleotides is selected to have a melting temperature ($T_m$) that differs from the melting temperatures of all other overlapping complementary oligonucleotides in a group consisting of the first and second sets of oligonucleotides; and
  (c) hybridising the first and second set of oligonucleotides.

The term "corresponding", in the context of corresponding to a strand of the polynucleotide, refers to the oligonucleotides providing all or part of the sequence of the strand, "corresponding" to an entire strand refers to the oligonucleotides providing the entire sequence of the strand when positioned together end-to-end.

The individual oligonucleotides comprising the group may be provided using any suitable means, such as a method of oligonucleotide synthesis disclosed herein.

In a preferred embodiment, the entire group of oligonucleotides are admixed together before the hybridising step. In another embodiment, the oligonucleotides are admixed in subsets, which are hybridised separately, and the subsets are then admixed together and hybridised.

In another embodiment, the entire group of oligonucleotides are admixed together before the hybridising step. In another preferred embodiment, the oligonucleotides are admixed in subsets, which are hybridised separately, and the subsets are then admixed together and hybridised.

In a preferred embodiment, the concentrations of each oligonucleotide are substantially balanced. Put another way, when the oligonucleotides are mixed, the pool of oligonucleotides preferably comprises substantially equal concentrations of each oligonucleotide.

In one embodiment, the oligonucleotides are 5' phosphorylated before the hybridising step. 5' phosphorylation may be carried out by, for example, treating the oligonucleotides with T4 polynucleotide kinase.

In a preferred embodiment, the hybridising comprises annealing the oligonucleotides.

The term "annealing" as used herein refers to the process of decreasing the temperature of an entity, typically from a relatively high temperature, over a period of time. Annealing a mixture of oligonucleotides may be achieved, for example, by heating the mixture to a desired temperature and then allowing the mixture to cool. During the annealing, the temperature may be decreased continuously (e.g. by allowing the mixture to cool naturally) or the temperature may be decreased in a plurality of steps.

Hybridising oligonucleotides may be carried out under any suitable conditions. For example, a 100 mM potassium acetate; 30 mM HEPES, pH 7.5 solution may be used to provide suitable buffering and salt conditions for hybridisation.

An example method for annealing a group of oligonucleotides is:
  1. Resuspend: dissolve each oligonucleotide in a suitable buffer (e.g. 100 mM potassium acetate; 30 mM HEPES, pH 7.5/Tris-HCl, pH 7.5); the oligonucleotides may be, for example, resuspended at a concentration of 10-100 µM;
  2. Mix: combine the oligonucleotides, preferably in equal molar amounts; and
  3. Anneal: heat the mixture of oligonucleotides, for example to about 95° C. for about 2 minutes and subsequently gradually cool (e.g. transfer the mixture to a bench-top at room temperature, or place the mixture in a water bath or heat block at about 95° C. and turn off the water bath or heat block).

In one embodiment, polymerase chain assembly is carried out on the group of oligonucleotides following the hybridisation step. The PCA may be used to add any omitted sequence regions of the double-stranded polynucleotide (i.e. corresponding to sequence gaps between neighbouring oligonucleotides). The PCA may be carried out, for example, using a nucleic acid polymerase (e.g. a DNA polymerase, such as a 5'-3' DNA polymerase).

In a preferred embodiment, the group of oligonucleotides are ligated following the hybridisation step. For example, the group of oligonucleotides may be treated with T4 DNA ligase or topoisomerase to ligate the oligonucleotides. Optionally, the oligonucleotides may be phosphorylated before ligation if required, for example using a polynucleotide kinase, such as T4 polynucleotide kinase.

In one embodiment, the polynucleotide provided by the method of the invention is amplified. For example, the polynucleotide may be amplified using the polymerase chain reaction (PCR).

In one embodiment, the polynucleotide provided by the method of the invention is transformed or transfected into a host cell. The host cell may be, for example, a bacterial, animal or plant cell.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1

Nucleic acid structures will naturally assemble from component oligonucleotides representing sections of the opposing (e.g. sense and anti-sense) strands.

This is exemplified by FIG. 1, which depicts a double-stranded DNA comprised of 9 oligonucleotides. Each strand is comprised of a number of separate oligonucleotides, which are represented by differing text formats (plain text, underline, bold and/or italic). The top strand is comprised of 5 oligonucleotides (A1-A5) and the bottom strand is comprised of 4 oligonucleotides (B1-B4).

At a sufficiently low temperature, all oligonucleotides will assemble at the same time leading to potential errors.

By intelligently selecting the overlapping regions of the oligonucleotides of the opposing strands, a spread of melting temperatures ($T_m$) can be achieved, for example by taking into account variations in overlap length and content.

A group of oligonucleotides designed in this manner will undergo sequential assembly of a nucleic acid structure, rather than simultaneous assembly, when occurring in a temperature-controlled environment. This controlled assembly mitigates errors occurring during self-assembly.

This approach has been exemplified using the "eukaryotic" green fluorescent protein (GFP), which is encoded by the following example nucleic acid sequence:

(SEQ ID NO: 1)
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAG

This nucleic acid sequence was analysed to find a solution group of oligonucleotides that will enable sequential self-assembly of its double-stranded polynucleotide form in a temperature-controlled manner.

The following criteria were established as the parameters for the search for a solution:
- Maximum oligonucleotide length: ≤200
- Minimum oligonucleotide length: ≥4
- Minimum melt point considered: 10° C.
- Maximum melt point considered: 90° C.
- Minimum delta between melt temperature points: 1° C.

The following additional optional criteria were also adopted to give structure to the search:
- Ideal delta between melt temperature points: 5° C.

The search was then carried out using the following algorithm:
1. Divide the temperature range into n points by having a point at each ideal delta increment (as shown below, the order of this list is significant):
   [90, 85, 80, 75, 70, 65, 60, 55, 50, 45, 40, 35, 30, 25, 20, 15, 10]° C.
2. Break up the target sequence (SEQ ID NO: 1) into overlap regions from the 3' direction, such that the melt temperature is as close to 90° C. as possible.
3. Repeat step 2, targeting the next melt temperature point in the list established in step 1 (i.e. 85° C., then 80° C., 75° C.) and so on until all melt temperature points in the list established in step 1 have an overlap associated with them.
4. Calculate the spread of melt temperatures in the solution and stop if it satisfies the previously established criteria.
5. If no satisfactory solution is found, reorder the list systematically and repeat the algorithm until either all list orders are exhausted or a solution is found.

This yielded 355687428096000 possible solutions for SEQ ID NO: 1. However, it was only necessary to look for the first solution that satisfies the previously described criteria.

Melt temperatures were calculated using the BioPython library implementation of the Wallace "Rule of Thumb" method, i.e. using the formula:

$$T_m = 4 \times (G+C) + 2 \times (A+T)$$

The first acceptable solution yields the following result. Below are described the oligonucleotides forming the opposing strands that together will form the target sequence whilst also achieving the spread of melt temperatures shown in FIG. 2.

Sense:
1.
(SEQ ID NO: 2)
5'-ATGGTGAGCAAGGGCGAGGAGCTGTTCACCGGGGTGGTGCCCATCCT

GGTCGAGCTGGACGGCGACGTAAACGGCCACAAGTTCAGCGTGTCCGGCG

AGGGCGAGGGCGATGCCACCTACGGCAAGCTGACCCTGAAGTTCATCTGC

ACCACCGGCAAGCTGCCC-3'

2.
(SEQ ID NO: 3)
5'-GTGCCCTGGCCCACCC-3'

3.
(SEQ ID NO: 4)
5'-TCGTGACCACCCTGACCTA-3'

4.
(SEQ ID NO: 5)
5'-CGGCGTGCAGTGCTTCA-3'

5.
(SEQ ID NO: 6)
5'-GCCGCTACCCCGACCACATGAAGCAGC-3'

6.
(SEQ ID NO: 7)
5'-ACGACTTCTTCAAGTCCGCCATGCCCGAAGGCTACG-3'

7.
(SEQ ID NO: 8)
5'-TCCAGGAGCGCACCATCTTCTTCAAGGACGACGGCAACTACAAGACC

CGCG-3'

8.
(SEQ ID NO: 9)
5'-CCGAGGTGAAGTTCGAGGGCGACACCCTGGTGAACCGCATCGAGCTG

AAGGGCATCGACTTCAAGGAGGACGGCAACATCCTGGGGCACAAGCTGG-

3'

9.
(SEQ ID NO: 10)
5'-AGTACAACTACAACAGCCACAACGTCTATATCATGGCCGACAAGCAG

AAGAACGGCATCAAGGTGAACTTCAAGATCCGCCACAACATCGAGGACGG

CAGCGTGCAGCTCGCCGACCACTACCAGCAGAACACCCCCATCGGCGACG

GCCCCGTGCTGCTGCCCGACAACCACTACCTGAGCACCCAGTC-3'

10.
(SEQ ID NO: 11)
5'-CGCCCTGAGCAAAGACCCCAACGAGAAGCGCGATCACATGGTCCTGC

TGGAGTTCGTGACCGCCGCGGGATCACTCTCGGCATGGACGAGCTGTAC

AAG-3'

Anti-sense:
1.
(SEQ ID NO: 12)
3'-TACCACTCGTTCCCGCTCCTCGACAAGTGGCCCCACCACGGGTAGGA

CCAGCTCGACCTGCCGCTGCATTTGCCGGTGTTCAAGTCGCACAGGCCGC

TCCCGCTCCCGCTACGGTGGATGCCGTTCGACTGGGACTTCAAGTAGACG

TGGTGGCCGTTCGACGGGCACGGGAC-5'

2.
(SEQ ID NO: 13)
3'-CGGGTGGGAGCACTGG-5'

3.
(SEQ ID NO: 14)
3'-TGGGACTGGATGCCGCACGT-5'

4.
(SEQ ID NO: 15)
3'-CACGAAGTCGGCGATGGGG-5'

5.
(SEQ ID NO: 16)
3'-CTGGTGTACTTCGTCGTGCTGAAGAAGTTCAGGC-5'

6.
(SEQ ID NO: 17)
3'-GGTACGGGCTTCCGATGCAGGTCCTCGCGTGGTAGAAGAAGTTC-5'

7.
(SEQ ID NO: 18)
3'-CTGCTGCCGTTGATGTTCTGGGCGCGGCTCCACTTCAAGCTCCCGCT

GTGGGACCACTTG-5'

8.
(SEQ ID NO: 19)
3'-GCGTAGCTCGACTTCCCGTAGCTGAAGTTCCTCCTGCCGTTGTAGGA

CCCCGTGTTCGACCTCATGTTGATGTTGTCGGTGTTGCAGATATAGTACC

GGCTGTTCGTCTTCTTGCCGTAGTTCCACTTGAAGTTCTAGGCGGTGTTG

TAGC-5'

9.
(SEQ ID NO: 20)
3'-TCCTGCCGTCGCACGTCGAGCGGCTGGTGATGGTCGTCTTGTGGGGG

TAGCCGCTGCCGGGGCACGACGACGGGCTGTTGGTGATGGACTCGTGGGT

CAGGCGGGACTCGTTTCTGGGGTTGCTCTTCGCGCTAGTGTACCAGGACG

ACCTCAAGCACTGGCGGCGGCCCTAGTGAGAGCCGTACCTGCTCGACATG

TTC-5'

As can be seen, there are 17 points at which the constituent oligonucleotides combine.

Figure 2:
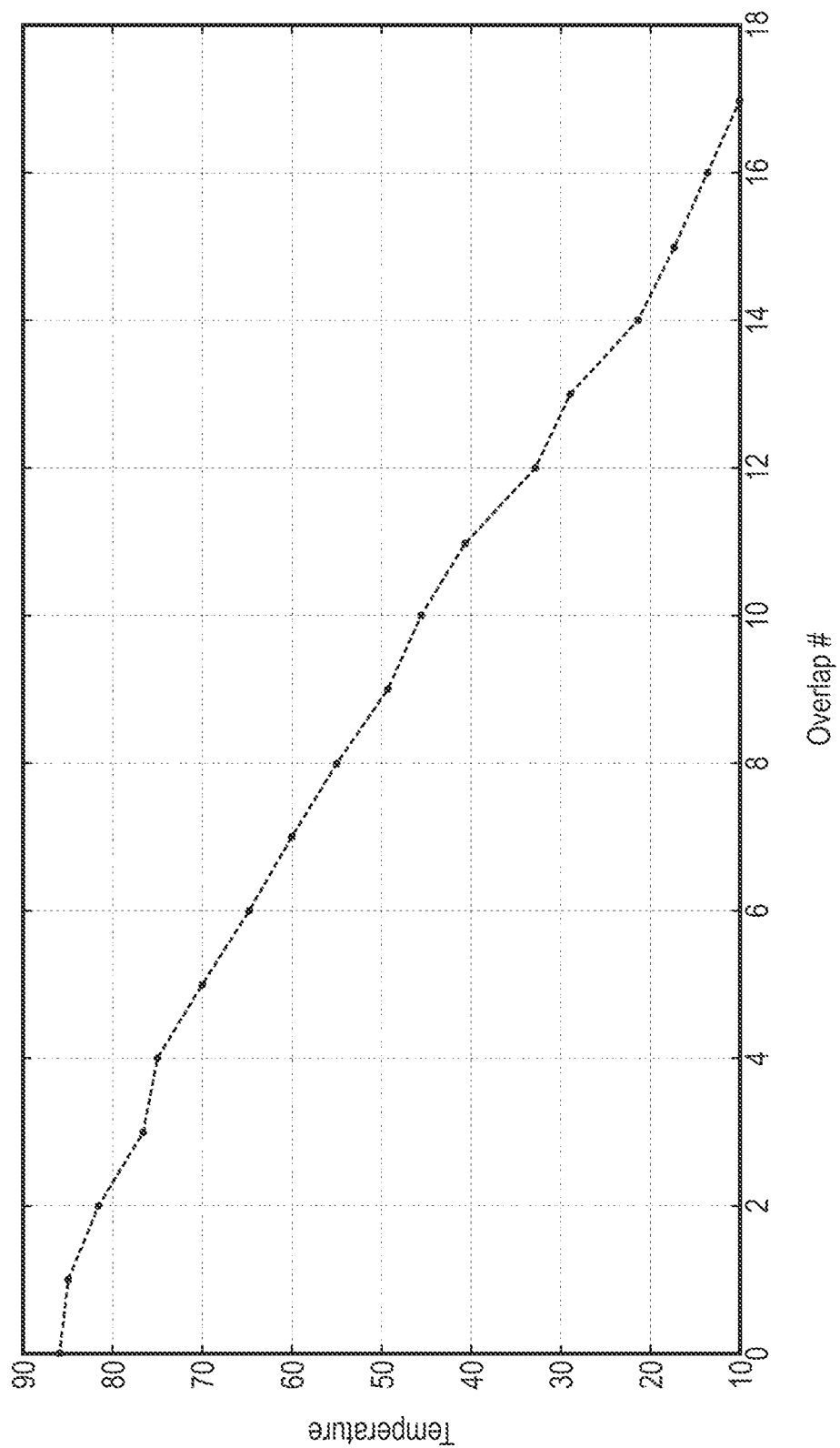

This group of oligonucleotides provides the spread of melt temperatures shown in FIG. 2.

The invention is further described by the following numbered paragraphs:

1. A method for identifying a group of single-stranded oligonucleotides for self-assembly into a double-stranded polynucleotide, the group comprising a plurality of overlapping complementary oligonucleotides, wherein each overlap between complementary oligonucleotides is selected to have a melting temperature ($T_m$) that differs from the melting temperatures of all other overlapping complementary oligonucleotides in the group.

2. A method for identifying a group of single-stranded oligonucleotides for assembly into a double-stranded polynucleotide comprising the steps:
   (a) dividing one strand of the polynucleotide to form a first set of oligonucleotides; and
   (b) dividing the opposite strand of the polynucleotide to form a second set of oligonucleotides;
   wherein each of the oligonucleotides of the second set of oligonucleotides overlaps with two oligonucleotides of the first set of oligonucleotides, except that two oligonucleotides at a 5' or 3' end of the double-stranded polynucleotide overlaps with only one complementary oligonucleotide, and wherein each overlap between complementary oligonucleotides is selected to have a melting temperature ($T_m$) that differs from the melting temperatures of all other overlapping complementary oligonucleotides in the group.

3. A method for providing multiple copies of a double-stranded polynucleotide comprising the steps:
   (a) providing a group of oligonucleotides identified using the method of paragraph 1 or 2; and
   (b) hybridising the oligonucleotides.

4. A method for providing multiple copies of a double-stranded polynucleotide comprising the steps:
   (a) providing a first set of oligonucleotides corresponding to one strand of the polynucleotide, preferably corresponding to one entire strand; and
   (b) providing a second set of oligonucleotides corresponding to the opposite strand of the polynucleotide, preferably corresponding to the entire opposite strand,
   wherein each of the oligonucleotides of the second set of oligonucleotides overlaps with two oligonucleotides of the first set of oligonucleotides, except that two oligonucleotides at a 5' or 3' end of the double-stranded polynucleotide overlaps with only one complementary oligonucleotide, and
   wherein each overlap between complementary oligonucleotides is selected to have a melting temperature ($T_m$) that differs from the melting temperatures of all other overlapping complementary oligonucleotides in a group consisting of the first and second sets of oligonucleotides; and
   (c) hybridising the first and second set of oligonucleotides.

5. The method of paragraph 3 or 4, wherein the hybridising comprises decreasing the temperature from a starting temperature over a period of time, preferably wherein the starting temperature is greater than or equal to the highest $T_m$, preferably wherein the starting temperature is greater than the highest $T_m$.

6. The method of any one of paragraphs 3-5, wherein the hybridising comprises decreasing the temperature from a temperature greater than or equal to the highest $T_m$ to a temperature less than or equal to the lowest $T_m$, preferably wherein the hybridising comprises decreasing the temperature from a temperature greater than the highest $T_m$ to a temperature less than the lowest $T_m$.

7. The method of paragraph 5 or 6, wherein the temperature is decreased continuously or in a plurality of steps.

8. The method of any one of paragraphs 3-7 further comprising the step of admixing the entire group of oligonucleotides before the hybridising step; or further comprising the step of admixing subsets of oligonucleotides, which are hybridised separately, and the subsequent step of admixing the subsets together and then hybridising the mixture of subsets.

9. The method of any preceding paragraph, wherein the oligonucleotides are less than or equal to about 200 nucleotides in length.

10. The method of any preceding paragraph, wherein the oligonucleotides are greater than or equal to about 4 nucleotides in length.

11. The method of any preceding paragraph, wherein the overlaps are selected to provide a highest $T_m$ of less than or equal to about 95° C.

12. The method of any preceding paragraph, wherein the overlaps are selected to provide a lowest $T_m$ of greater than or equal to about 10° C.

13. The method of any preceding paragraph, wherein each overlap is selected to provide a difference between its $T_m$ and the closest higher and/or lower $T_m$ of greater than or equal to about 0.5° C., preferably about 0.5-10° C., more preferably about 4-6° C.

14. The method of any one of paragraphs 3-13, wherein the oligonucleotides are synthesised in vitro.

15. The method of any one of paragraphs 3-14 further comprising the steps:
   (d) polymerase chain assembly (PCA);
   (e) treating the hybridised oligonucleotides with a ligase and optionally a polynucleotide kinase; and/or
   (f) amplifying the double-stranded polynucleotide.

16. The method of any preceding paragraph, wherein the double-stranded polynucleotide is a DNA, RNA or XNA.

17. The method of any preceding paragraph, wherein the double-stranded polynucleotide comprises a coding region.

18. The method of any preceding paragraph, wherein the double-stranded polynucleotide comprises an expression construct, chromosome or genome.

19. The method of paragraph 18, wherein the expression construct is a bacterial, mammalian or viral expression construct.

20. The method of any preceding paragraph, wherein the number of errors in assembly of the polynucleotide due to hybridising of non-complementary oligonucleotides is reduced in comparison to a method in which each overlap between complementary oligonucleotides is not selected to have a melting temperature ($T_m$) that differs from the melting temperatures of all other overlapping complementary oligonucleotides in the group.

21. A group of single-stranded oligonucleotides for self-assembly into a double-stranded polynucleotide, the group comprising a plurality of overlapping complementary oligonucleotides, wherein each overlap between complementary oligonucleotides is selected to have a melting temperature ($T_m$) that differs from the melting temperatures of all other overlapping complementary oligonucleotides in the group.

22. The group of single-stranded oligonucleotides of paragraph 21, wherein the oligonucleotides and/or overlaps are as defined in any one of paragraphs 9-14.

23. A double-stranded polynucleotide produced by the method of any one of paragraphs 3-20.

24. The method of any one of paragraphs 1-20, wherein the selection of the oligonucleotides is carried out by a computer.

25. A data processing device comprising means for carrying out the method of any one of paragraphs 1, 2, 9-13 or 16-20.

26. A computer program product in which a computer program is stored in a non-transient fashion, which when executed on a processing device causes the processing device to carry out the method of any one of paragraphs 1, 2, 9-13 or 16-20.

27. A computer-readable medium comprising instructions which, when executed by a computer, cause the computer to carry out the method of any one of paragraphs 1, 2, 9-13 or 16-20.

All publications mentioned in the above specification are herein incorporated by reference. Various modifications and variations of the disclosed methods, products and devices of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. A method for producing a double-stranded polynucleotide, wherein the method comprises the steps:
   (a) selecting and providing a group of single-stranded oligonucleotides for self-assembly into the double-stranded polynucleotide, the group comprising a plurality of overlapping complementary oligonucleotides, wherein each overlap between complementary oligonucleotides is selected to have a melting temperature ($T_m$) that differs from the melting temperatures of all other overlapping complementary oligonucleotides in the group, and wherein each overlap is selected to provide a difference between its $T_m$ and the closest higher and lower $T_m$ of greater than or equal to 2° C. as determined by nearest-neighbour model; and
   (b) producing the double-stranded polynucleotide by self-assembly of the group of single-stranded oligonucleotides.

2. The method of claim 1, wherein the oligonucleotides are less than or equal to about 200 nucleotides in length and/or wherein the oligonucleotides are greater than or equal to about 4 nucleotides in length.

3. The method of claim 1, wherein the overlaps are selected to provide a highest $T_m$ of less than or equal to about 95° C. and/or wherein the overlaps are selected to provide a lowest $T_m$ of greater than or equal to about 10° C.

4. The method of claim 1, wherein the double-stranded polynucleotide:
   (a) is a DNA, RNA or XNA;
   (b) comprises a coding region; and/or
   (c) comprises an expression construct, chromosome or genome.

5. The method of claim 1, wherein the number of errors in assembly of the polynucleotide due to hybridising of non-complementary oligonucleotides is reduced in comparison to a method in which each overlap between complementary oligonucleotides is not selected to have a melting temperature ($T_m$) that differs from the melting temperatures of all other overlapping complementary oligonucleotides in the group.

6. The method of claim 1, wherein the selection of the oligonucleotides is carried out by a computer.

7. The method of claim 1, wherein the providing a group of single-stranded oligonucleotides comprises the steps:
   (i) dividing one strand of the polynucleotide to form a first set of oligonucleotides; and
   (ii) dividing the opposite strand of the polynucleotide to form a second set of oligonucleotides;
   wherein each of the oligonucleotides of the second set of oligonucleotides overlaps with two oligonucleotides of the first set of oligonucleotides, except that two oligonucleotides at a 5' or 3' end of the double-stranded polynucleotide overlaps with only one complementary oligonucleotide.

8. The method of claim 1, wherein step (b) comprises hybridizing the single-stranded oligonucleotides to produce multiple copies of the double-stranded polynucleotide.

9. The method of claim 8, wherein the hybridizing comprises decreasing the temperature from a starting temperature over a period of time, and/or wherein the hybridizing comprises decreasing the temperature from a temperature greater than or equal to the highest $T_m$ to a temperature less than or equal to the lowest $T_m$.

10. The method of claim 8, further comprising the step of admixing the entire group of single-stranded oligonucleotides before the hybridizing step; or further comprising the step of admixing subsets of oligonucleotides, which are hybridized separately, and the subsequent step of admixing the subsets together and then hybridizing the mixture of subsets.

11. The method of claim 8, further comprising the steps:
   (i) polymerase chain assembly (PCA);
   (ii) treating the hybridized oligonucleotides with a ligase and optionally a polynucleotide kinase; and/or
   (iii) amplifying the double-stranded polynucleotide.

12. The method of claim 1, wherein each overlap is selected to provide a difference between its $T_m$ and the closest higher and lower $T_m$ of greater than or equal to 3° C.

13. A method for providing multiple copies of a double-stranded polynucleotide comprising the steps:
   (a) selecting and providing a first set of oligonucleotides corresponding to one strand of the polynucleotide; and
   (b) selecting and providing a second set of oligonucleotides corresponding to the opposite strand of the polynucleotide, wherein each of the oligonucleotides of the second set of oligonucleotides overlaps with two oligonucleotides of the first set of oligonucleotides, except that two oligonucleotides at a 5' or 3' end of the double-stranded polynucleotide overlaps with only one complementary oligonucleotide, and wherein each overlap between complementary oligonucleotides is selected to have a melting temperature ($T_m$) that differs from the melting temperatures of all other overlapping complementary oligonucleotides in a group consisting of the first and second sets of oligonucleotides, and wherein each overlap is selected to provide a difference between its $T_m$ and the closest higher and lower $T_m$ of greater than or equal to 2° C. as determined by nearest-neighbour model; and (c) hybridising the first and second set of oligonucleotides.

14. The method of claim 13, wherein the hybridising comprises decreasing the temperature from a starting temperature over a period of time, and/or wherein the hybridising comprises decreasing the temperature from a temperature greater than or equal to the highest $T_m$ to a temperature less than or equal to the lowest $T_m$.

15. The method of claim 13, further comprising the step of admixing the entire group of oligonucleotides before the hybridising step; or further comprising the step of admixing subsets of oligonucleotides, which are hybridised separately, and the subsequent step of admixing the subsets together and then hybridising the mixture of subsets.

* * * * *

SEQUENCE LISTING

<160> NUMBER OF SEQ ID NOS: 22

<210> SEQ ID NO 1
<211> LENGTH: 717
<212> TYPE: DNA
<213> ORGANISM: Artificial Sequence
<220> FEATURE:
<223> OTHER INFORMATION: Example sequence for eukaryotic green
      fluorescent protein, GFP

<400> SEQUENCE: 1

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaag      717
```

<210> SEQ ID NO 2
<211> LENGTH: 165
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 2

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgccc                   165
```

<210> SEQ ID NO 3
<211> LENGTH: 16
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 3

```
gtgccctggc ccaccc                                                    16
```

<210> SEQ ID NO 4
<211> LENGTH: 19
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 4

```
tcgtgaccac cctgaccta                                                 19
```

```
<210> SEQ ID NO 5
<211> LENGTH: 17
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 5
cggcgtgcag tgcttca                                                    17

<210> SEQ ID NO 6
<211> LENGTH: 27
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 6
gccgctaccc cgaccacatg aagcagc                                         27

<210> SEQ ID NO 7
<211> LENGTH: 36
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 7
acgacttctt caagtccgcc atgcccgaag gctacg                               36

<210> SEQ ID NO 8
<211> LENGTH: 51
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 8
tccaggagcg caccatcttc ttcaaggacg acggcaacta caagacccgc g              51

<210> SEQ ID NO 9
<211> LENGTH: 96
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 9
ccgaggtgaa gttcgagggc gacaccctgg tgaaccgcat cgagctgaag ggcatcgact     60
tcaaggagga cggcaacatc ctggggcaca agctgg                               96

<210> SEQ ID NO 10
<211> LENGTH: 190
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 10
```
agtacaacta caacagccac aacgtctata tcatggccga caagcagaag aacggcatca    60
aggtgaactt caagatccgc cacaacatcg aggacggcag cgtgcagctc gccgaccact   120
accagcagaa cacccccatc ggcgacggcc ccgtgctgct gcccgacaac cactacctga   180
gcacccagtc                                                         190

<210> SEQ ID NO 11
<211> LENGTH: 100
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 11
cgccctgagc aaagacccca acgagaagcg cgatcacatg gtcctgctgg agttcgtgac    60
cgccgccggg atcactctcg gcatggacga gctgtacaag                        100

<210> SEQ ID NO 12
<211> LENGTH: 173
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 12
cagggcacgg gcagcttgcc ggtggtgcag atgaacttca gggtcagctt gccgtaggtg    60
gcatcgccct cgccctcgcc ggacacgctg aacttgtggc cgtttacgtc gccgtccagc   120
tcgaccagga tgggcaccac cccggtgaac agctcctcgc ccttgctcac cat         173

<210> SEQ ID NO 13
<211> LENGTH: 16
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 13
ggtcacgagg gtgggc                                                   16

<210> SEQ ID NO 14
<211> LENGTH: 20
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 14
tgcacgccgt aggtcagggt                                               20

<210> SEQ ID NO 15
<211> LENGTH: 19
<212> TYPE: DNA
<213> ORGANISM: Artificial Sequence
<220> FEATURE:
<223> OTHER INFORMATION: oligonucleotide for sequential self-assembly of
      nucleic acid sequence

<400> SEQUENCE: 15
ggggtagcgg ctgaagcac                                                19

<210> SEQ ID NO 16
<211> LENGTH: 34
<212> TYPE: DNA
<213> ORGANISM: Artificial Sequence
<220> FEATURE:
<223> OTHER INFORMATION: oligonucleotide for sequential self-assembly of
    nucleic acid sequence

<400> SEQUENCE: 16
cggacttgaa gaagtcgtgc tgcttcatgt ggtc                                34

<210> SEQ ID NO 17
<211> LENGTH: 44
<212> TYPE: DNA
<213> ORGANISM: Artificial Sequence
<220> FEATURE:
<223> OTHER INFORMATION: oligonucleotide for sequential self-assembly of
    nucleic acid sequence

<400> SEQUENCE: 17
cttgaagaag atggtgcgct cctggacgta gccttcgggc atgg                     44

<210> SEQ ID NO 18
<211> LENGTH: 60
<212> TYPE: DNA
<213> ORGANISM: Artificial Sequence
<220> FEATURE:
<223> OTHER INFORMATION: oligonucleotide for sequential self-assembly of
    nucleic acid sequence

<400> SEQUENCE: 18
gttcaccagg gtgtcgccct cgaacttcac ctcggcgcgg gtcttgtagt tgccgtcgtc    60

<210> SEQ ID NO 19
<211> LENGTH: 151
<212> TYPE: DNA
<213> ORGANISM: Artificial Sequence
<220> FEATURE:
<223> OTHER INFORMATION: oligonucleotide for sequential self-assembly of
    nucleic acid sequence

<400> SEQUENCE: 19
cgatgttgtg gcggatcttg aagttcacct tgatgccgtt cttctgcttg tcggccatga    60
tatagacgtt gtggctgttg tagttgtact ccagcttgtg ccccaggatg ttgccgtcct   120
ccttgaagtc gatgcccttc agctcgatgc g                                  151

<210> SEQ ID NO 20
<211> LENGTH: 200
<212> TYPE: DNA
<213> ORGANISM: Artificial Sequence
<220> FEATURE:
<223> OTHER INFORMATION: oligonucleotide for sequential self-assembly of
    nucleic acid sequence

<400> SEQUENCE: 20
cttgtacagc tcgtccatgc cgagagtgat cccggcggcg gtcacgaact ccagcaggac    60
catgtgatcg cgcttctcgt tggggtcttt gctcagggcg gactgggtgc tcaggtagtg   120
gttgtcgggc agcagcacgg ggccgtcgcc gatggggtg ttctgctggt agtggtcggc   180
gagctgcacg ctgccgtcct                                               200

<210> SEQ ID NO 21
<211> LENGTH: 40
<212> TYPE: DNA

```
<213> ORGANISM: Artificial Sequence
<220> FEATURE:
<223> OTHER INFORMATION: Example double-stranded DNA

<400> SEQUENCE: 21
gaacatgtcg agcaggtacg gctctcacta gggccgccgc                        40

<210> SEQ ID NO 22
<211> LENGTH: 40
<212> TYPE: DNA
<213> ORGANISM: Artificial Sequence
<220> FEATURE:
<223> OTHER INFORMATION: Example double-stranded DNA

<400> SEQUENCE: 22
gcggcggccc tagtgagagc cgtacctgct cgacatgttc                        40
```